United States Patent [19]

Saville

[11] Patent Number: Plant 7,757

[45] Date of Patent: Dec. 31, 1991

[54] MINIATURE ROSE PLANT NAME SAVADREAM

[75] Inventor: F. Harmon Saville, Rowley, Mass.

[73] Assignee: Nor'East Miniature Roses, Inc., Rowley, Mass.

[21] Appl. No.: 570,520

[22] Filed: Aug. 21, 1990

[51] Int. Cl.[5] ..... A01H 5/00

[52] U.S. Cl. ..... Plt./9

[58] Field of Search ..... Plt. 9

*Primary Examiner*—James R. Feyrer

*Attorney, Agent, or Firm*—Christie, Parker & Hale

[57] ABSTRACT

A new and unusual miniature rose producing dusty pink flowers.

SUMMARY OF THE INVENTION

The present invention relates to a new and distinct variety of rose plant of the miniature rose class, which was originated by my crossing as seed parent the variety known as "Baby Katie" (U.S. Pat. No. 4,471) and as pollen parent the variety known as "Shocking Blue" (U.S. Pat. No. 3,846). The varietal denomination of this new rose is "Savadream".

Among the novel characteristics possessed by this new variety which distinguishes if from its parents and all other varieties if which I am aware are its unusual clear, dusty pink flowers in this class of rose. Flowers open well and have deeper toned pink coloration on the reverse side of the petals.

Asexual reproduction by propagation by cuttings of the new variety as performed in Essex County, Mass. shows that the foregoing and other distinguishing characteristics come true to form and are established and transmited through succeeding propagations.

1 Drawing Sheet

BRIEF DESCRIPTION OF DRAWING

The accompanying drawing shows typical specimens of the vegetative growth and flowers of the new variety in different stages of development and depicted in color as nearly true as it is reasonably possible to make the same in a color illustration of this character.

DESCRIPTION OF THE PREFERRED EMBODIMENT

The following is a detailed description of my new variety, with color terminology in accordance with The Royal Horticultural Society Colour Chart (R.H.S.C.C.). The terminology used in color description herein refers to plate numbers in the aforementioned color chart, e.g., "55B" is plate "55B" of The Royal Horticultural Society Colour Chart.

Parentage: Seedling.

*Seed parent.*—"Baby Katie".

*Pollen parent.*—"Shocking Blue".

Class: Miniature.

The following observations are made of specimens grown under glass in Essex County, Mass., during the month of May.

Flower

Blooming habit: Recurrent, continuous.

A. Bud:

(1) *Size.*—Medium.

(2) *Form.*—Urn shaped.

(3) *Color.*—As sepals divide, bud color is near 55B.

(4) *Sepals.*—Longer than bud, very lightly foliated.

(5) *Penduncle.*—Length — about 1 inch. Aspect — straight. Strength — erect. Color — near 144A.

B. Bloom:

(1) *Size.*—Average size when fully expanded — about 1⅝ inches.

(2) *Borne.*—Singly, one to a stem and in sprays of 3 to 5 blooms.

(3) *Form.*—High centered at first, becoming flat; petals remaining at first loosely rolled outward.

(4) *Petalage.*—Number of petals under normal conditions — about 20.

(5) *Color.*—After sepals fall and petals unfurl, predominant flower color viewing petals' top surface is from near 55C and D to 56A to D. Color of petal undersurface is from near 55A to 55B. Viewing flower from the top, the coloration appears deeper toned where petals bunch. Flower coloring is clean and constant. General tonality at a distance is a pleasant dusty pink which tends to lighten as flowers age. Color of at point of petal attachment is near 2D.

C. Petals:

(1) *Texture.*—Average.

(2) *Appearance.*—Satiny.

(3) *Form.*—Broad, fan shaped with smooth margin.

(4) *Arrangement.*—Regularly arranged, imbricated.

(5) *Petaloids in center.*—Few.

(6) *Persistence.*—Drop off cleanly.

(7) *Fragrance.*—None.

(8) *Lasting quality.*—Average lasting quality on plant and as cut flower.

REPRODUCTIVE ORGANS

A. Stamens, filaments and anthers:

*Arrangement and color.*—Regularly arranged around styles. Color — filaments near 16A.

B. Pollen:

*Color.*—Near 16A.

C. Styles: Even length.

D. Stigmas:

*Color.*—Near 2D.

E. Hips: None observed.

PLANT

A. Form: Upright, compact.

B. Growth: Very vigorous, uniform branching.
*Height attained.*—About 14 to 18 inches.

C. Foliage: Compound 5 to 7 leaflets.
(1) *Size.*—Medium.
(2) *Quantity.*—Abundant.
(3) *Color.*—New foliage: Upper side — near 146A. Under side — near 182B. Old foliage: Upper side — near 139A. Under side — near 138B.
(4) *Shape.*—Oval, pointed.
(5) *Texture.*—Upper side is semi-glossy; under side is matte.
(6) *Edge.*—Serrate.
(7) *Serration.*—Ordinary.
(8) *Leaf stem.*—Color — near 183C. Under side — 182B.
(9) *Stipules.*—Medium length, slightly bearded.
(10) *Resistance to disease.*—Blackspot — Average. Mildew — Average. Rust — Average.

D. Wood:
(1) *New wood.*—Color — near 191A. Bark — smooth.
(2) *Old wood.*—Color — near 191A. Bark — smooth.

E. Thorns:
*Quantity (main stalk).*—Few.
*On laterals from stalk.*—Few.
*Form.*—Slightly angled downward.
*Length.*—Medium.
*Color.*—Near 178A.
*Position.*—Irregular.
*Prickles.*—None.

F. Winter hardiness: Needs protection in severe climates.

I claim:

1. A new and distinct variety of rose plant of the miniature rose class, substantially as shown and described, characterized particularly by attractive dusty pink flowers.

* * * * *

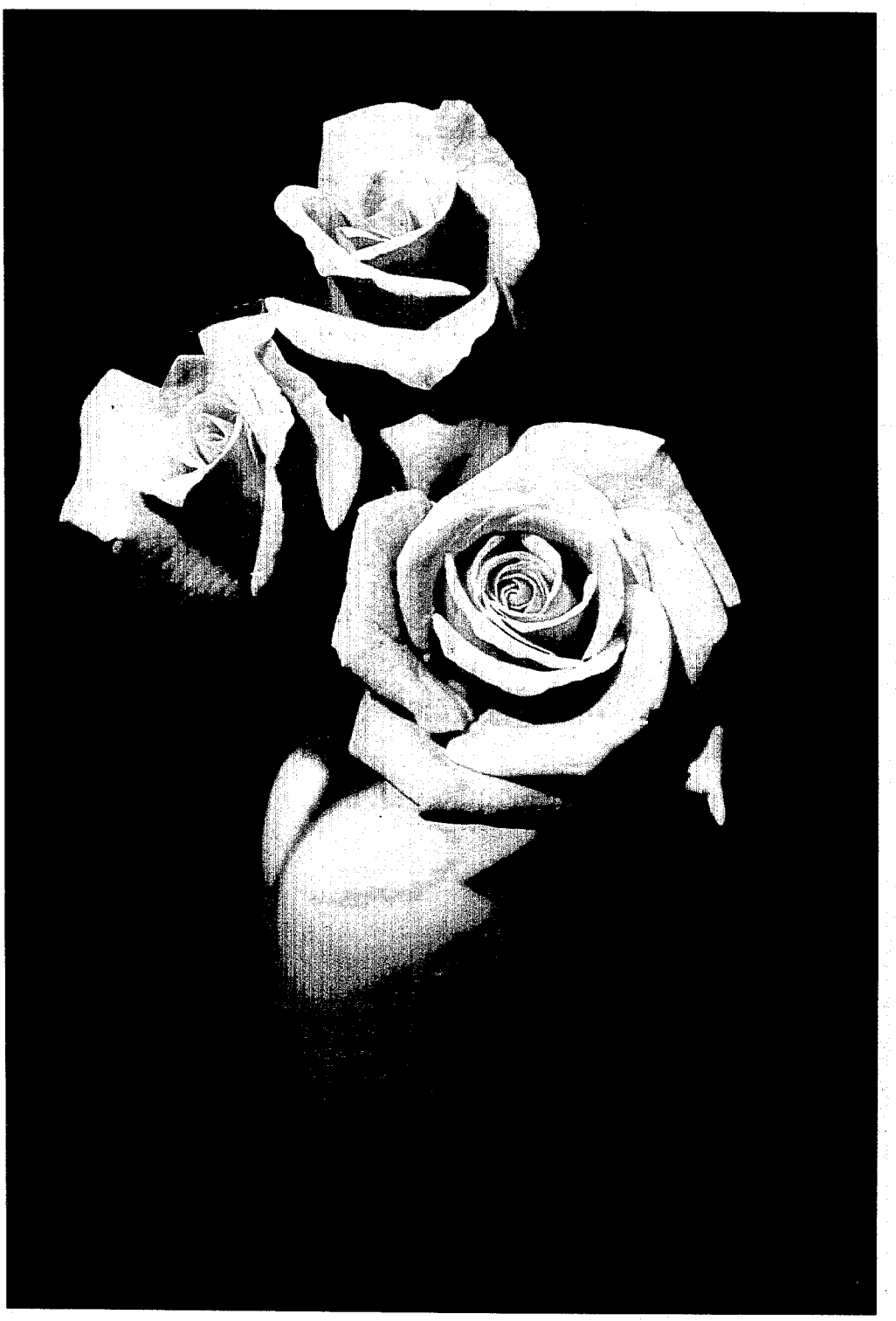

UNITED STATES PATENT AND TRADEMARK OFFICE

CERTIFICATE OF CORRECTION

PATENT NO. : Plant 7,757

DATED : December 31, 1991

INVENTOR(S) : F. Harmon Saville

It is certified that error appears in the above-identified patent and that said Letters Patent is hereby corrected as shown below:

Title page, item

[54] In the title, change "NAME" to -- NAMED --.
Move the entire section entitled "SUMMARY OF THE INVENTION" to Column 1.

Summary of the Invention, line 9, after "distinguishes" change "if" to -- it --.
Summary of the Invention, line 10, after "varieties" change "if" to -- of --.

In the Claims:

Column 4, line 18, delete "1.".

Signed and Sealed this

Thirteenth Day of July, 1993

*Attest:*

Michael K. Kirk

MICHAEL K. KIRK

*Attesting Officer*

*Acting Commissioner of Patents and Trademarks*